(12) United States Patent
Kaufmann

(10) Patent No.: US 10,828,147 B1
(45) Date of Patent: Nov. 10, 2020

(54) LIGAMENT RETENTION DEVICE

(71) Applicant: Robert A. Kaufmann, Pittsburgh, PA (US)

(72) Inventor: Robert A. Kaufmann, Pittsburgh, PA (US)

( * ) Notice: Subject to any disclaimer, the term of this patent is extended or adjusted under 35 U.S.C. 154(b) by 107 days.

(21) Appl. No.: 16/123,957

(22) Filed: Sep. 6, 2018

Related U.S. Application Data

(60) Provisional application No. 62/619,899, filed on Jan. 21, 2018.

(51) Int. Cl.
| | |
|---|---|
| *A61F 2/08* | (2006.01) |
| *A61F 2/38* | (2006.01) |
| *A61F 2/30* | (2006.01) |
| *A61F 2/46* | (2006.01) |

(52) U.S. Cl.
CPC .......... *A61F 2/0811* (2013.01); *A61F 2/0805* (2013.01); *A61F 2/30749* (2013.01); *A61F 2/3804* (2013.01); *A61F 2/4605* (2013.01); *A61F 2002/0817* (2013.01); *A61F 2002/30235* (2013.01); *A61F 2002/30405* (2013.01); *A61F 2002/30507* (2013.01)

(58) Field of Classification Search
CPC ........ A61F 2/08; A61F 2/0811; A61F 2/3804; A61F 2/0805; A61F 2/30749; A61F 2/3836; A61F 2002/0847; A61F 2002/0882; A61F 2002/0852; A61F 2002/0864; A61F 2002/087; A61B 17/0401; A61B 17/0466; A61B 17/0487; A61B 17/6425; A61B 17/567; A61B 17/1714; A61B 17/1725; A61B 17/1764; A61B 17/686; A61B 17/68; A61B 17/846

USPC ...................................................... 606/96–98
See application file for complete search history.

(56) References Cited

U.S. PATENT DOCUMENTS

| | | | |
|---|---|---|---|
| 2,696,817 | A | 12/1954 | Prevo |
| 3,547,115 | A | 12/1970 | Stevens |
| 3,708,805 | A | 1/1973 | Scales et al. |
| 3,772,709 | A | 11/1973 | Swanson |
| 3,816,854 | A | 6/1974 | Schlein |
| 3,852,831 | A | 12/1974 | Dee |
| 3,868,730 | A | 3/1975 | Kaufer et al. |
| 3,919,725 | A | 11/1975 | Swanson et al. |

(Continued)

OTHER PUBLICATIONS

Foruria AM, Sanchez-Sotelo J, Oh LS et al. The Surgical Treatment of Periprosthetic Elbow Fractures Around the Ulnar Stem Following Semiconstrained Total Elbow Arthroplasty, J-BJS 93.15 (2011) : 1399-1407.

(Continued)

*Primary Examiner* — Brian A Dukert
*Assistant Examiner* — Amanda M Barkan
(74) *Attorney, Agent, or Firm* — William F. Lang, IV; Lang Patent Law LLC

(57) ABSTRACT

A device for ligament reconstruction includes an elongated body and a hook or loop at each end for receiving a ligament reconstruction member such as an allograft or autograft tendon. The ligament reconstruction member is positioned within a hole that is drilled into a bone, or which is provided within a prosthetic joint. A central portion of a ligament reconstruction member is passed through each end of the device. The ends of the ligament reconstruction members are then fastened to the opposing bone forming the joint.

9 Claims, 13 Drawing Sheets

(56) References Cited

U.S. PATENT DOCUMENTS

| | | | |
|---|---|---|---|
| 3,939,496 | A | 2/1976 | Ling et al. |
| 3,990,117 | A | 11/1976 | Pritchard et al. |
| 3,991,425 | A | 11/1976 | Martin et al. |
| 4,008,495 | A | 2/1977 | Cavendish et al. |
| 4,057,858 | A | 11/1977 | Helfet |
| 4,079,469 | A | 3/1978 | Wadsworth |
| 4,129,902 | A | 12/1978 | Harmon |
| 4,131,956 | A | 1/1979 | Treace |
| 4,224,695 | A | 9/1980 | Grundei et al. |
| 4,242,758 | A | 1/1981 | Amis et al. |
| 4,280,231 | A | 7/1981 | Swanson |
| 4,293,963 | A | 10/1981 | Gold et al. |
| 4,383,337 | A | 5/1983 | Volz et al. |
| 4,538,306 | A | 9/1985 | Dorre et al. |
| 4,681,590 | A | 7/1987 | Tansey |
| 4,712,542 | A | 12/1987 | Daniel et al. |
| 4,840,633 | A | 6/1989 | Kallabis et al. |
| 5,167,666 | A | 12/1992 | Mattheck et al. |
| 5,282,867 | A | 2/1994 | Mikhail |
| 5,314,484 | A | 5/1994 | Huene |
| 5,376,121 | A | 12/1994 | Huene et al. |
| 5,458,654 | A | 10/1995 | Tepic |
| 5,520,693 | A | 5/1996 | McGuire et al. |
| 5,562,668 | A | 10/1996 | Johnson |
| 5,667,510 | A | 9/1997 | Combs |
| 5,723,015 | A | 5/1998 | Risung et al. |
| 5,782,923 | A | 7/1998 | Engelbrecht et al. |
| 5,879,395 | A | 3/1999 | Tornier et al. |
| 5,989,261 | A | 11/1999 | Walker et al. |
| 6,027,534 | A | 2/2000 | Wack et al. |
| 6,126,691 | A | 10/2000 | Kasra et al. |
| 6,162,253 | A | 12/2000 | Conzemius et al. |
| 6,290,725 | B1 | 9/2001 | Weiss et al. |
| 6,306,171 | B1 | 10/2001 | Conzemius |
| 6,325,804 | B1 | 12/2001 | Wenstrom, Jr. et al. |
| 6,379,387 | B1 | 4/2002 | Tornier |
| 6,475,242 | B1 | 11/2002 | Bramlet |
| 6,514,288 | B2 | 2/2003 | Meulink et al. |
| 6,517,541 | B1 | 2/2003 | Sesic |
| 6,533,802 | B2 * | 3/2003 | Bojarski ............ A61B 17/0401 606/228 |
| 6,699,290 | B1 | 3/2004 | Wack et al. |
| 6,716,248 | B2 | 4/2004 | Huene |
| 6,767,368 | B2 | 7/2004 | Tornier |
| 6,878,150 | B1 | 4/2005 | McGuire et al. |
| 6,890,357 | B2 | 5/2005 | Tornier |
| 6,905,513 | B1 | 6/2005 | Metzger |
| 6,949,102 | B2 | 9/2005 | Andrews |
| 6,997,957 | B2 | 2/2006 | Huene |
| 7,247,170 | B2 | 7/2007 | Graham et al. |
| 7,850,737 | B2 | 10/2010 | Morrey |
| 9,289,304 | B1 | 3/2016 | Kaufmann |
| 9,962,200 | B1 | 5/2018 | Kaufmann |
| 2005/0049710 | A1 | 3/2005 | O'Driscoll et al. |
| 2006/0052878 | A1 | 3/2006 | Schmieding |
| 2007/0185584 | A1 | 8/2007 | Kaufmann et al. |
| 2009/0125114 | A1 | 5/2009 | May et al. |
| 2009/0228017 | A1 | 9/2009 | Collins |
| 2010/0057214 | A1 | 3/2010 | Graham et al. |
| 2010/0179661 | A1 | 7/2010 | Berelsman et al. |
| 2010/0241239 | A1 | 9/2010 | Smith |
| 2011/0040339 | A1 | 2/2011 | Solomon et al. |
| 2012/0109322 | A1 | 5/2012 | Gonzalez-Hernandez |
| 2014/0277550 | A1 | 9/2014 | Lindsay et al. |

OTHER PUBLICATIONS

F. Akpinar et al., A Morphometric Study of the Humerus for Intramedullary Fixation, Tobuko J. Exp. Med. (2003) 199, 35-42.

Garrett JC, Ewald FC, Thomas WH et al. Loosening Associated with G.S.B. Hinge Total Elbow Replacement in Patients with Rheumatoid Arthritis, Clin Orthop Relat Res 1977; (127): 170-174.

Gschwend N, Simmen BR, Matejovsky Z. Late Complications in Elbow Arthroplasty, J Shoulder Elbow Surg 1996;5 (2 Pt 1):86-96.

G. Stein, O. Weber, K. J. Burkhart, and L. P. Muller, Ellenbogengelenk-Totalendoprothese, Der Unfallchirurg (2010) 1006-1012.

Hildebrand KA, Patterson SD, Regan WD et al. Functional Outcome of Semiconstrained Total Elbow Arthroplasty, J Bone Joint Surg Am 2000:82-A (10):1379-1386.

Hurri L, Pulkki T, Vainio K. Arthroplasty of the Elbow in Rheumatoid Arthritis, ACTA Chir Scand 964;127:459-465.

I. H. Jeon et al., Incidence and Implications of Early Postoperative Wound Complications After Total Elbow Anthroplasty, J. Shoulder and Elbow Surgery (2011), 20, 857-865.

Kai-Nan An, Kinematics and Constraint of Total Elbow Anthroplasty, J Shoulder Elbow Surg (2005) 14(15): 168S-173S.

Ken Yamaguchi, Robert A. Adams, and Bernard F. Morrey, Infection After Total Elbow Anthroplasty, J Bone Joint Surg, (1998) 80A (4) 481-491.

Kim JM, Mudgal CS, Konopka JF et al. Complications of Total Elbow Arthroplasty, J Am Acad Orthop Surg 2011;19 (6):328-339.

Lucie Krenek, Eugene Farng, David Zigmond, and Nelson F. SooHoo, Complication and Revision Rates Following Total Elbow Anthroplasty, JHS, (2011) 36A: 68-73.

Matthew P. Abdel and Bernard F. Morrey, Implications of Revision Total Elbow Anthroplasty on Blood Transfusion, J Shoulder Elbow Surg (2010) 19:190-195.

O'Driscoll SW, Morrey BF. Periprosthetic Fractures about the Elbow, Orthop Clin North Am 1999;30 (2):319-325.

P. S. Ray et al., Total Elbow Anthroplasty as Primary Treatment for Distal Humeral Fractures in Elderly Patients, Injury Int. J. Care Injured 31 (2000) 687-692.

J. Sanchez Sotelo et al., Periprosthetic Humeral Fractures After Total Elbow Anthroplasty, Journal of Bone and Joint Surgery (2002), 1642-1650.

Scott F. M. Duncan, John W. Sperling, and Bernard Morrey, Incidence and Risk Factors for Blood Transfusion in Total Elbow Anthroplasty, J Shoulder Elbow Surg (2008) 961-962.

Tachihara A, Nakamura H, Yoshioka T et al., Postoperative Results and Complications of Total Elbow Arthroplasty in Patients with Rheumatoid Arthritis: Three Types of Nonconstrained arthroplasty, Modern rheumatology 18.5 (2008): 465-471.

D. Tokunaga et al., Periprosthetic Ulnar Fracture After Loosening of Total Elbow Anthroplasty Treated by Two Stage Implant Revision, J. Shoulder Elbow Surg. Nov./Dec. 2006, 23-6.

Tyson K. Cobb and Bernard F. Morrey, Total Elbow Anthroplasty as Primary Treatment for Distal Humerus Fractures in Elderly Patients, J Bone Joint Surg (1997) 826-832.

Van der Heide HJ, de Vos MJ, Brinkman JM et al. Survivorship of the KUDO Total Ebow Prosthesis—Comparative Study of Cemented and Uncemented Ulnar Components: 89 Cases Follow.

Zinon T. Kokkalis, Christopher C. Schmidt, and Dean G. Sotereanos, Elbow Arthritis: Current Concepts, JHS (2009) 34A: 761-768.

Acclaim Total Elbow System, DePuy Orthopaedics, Inc., 2004.

Biomet Lateral Resurfacing Elbow, Biomet Orthopedics, Inc.

Discovery Elbow System, Biomet Orthopedics, Inc.

Instrumental Bone Preserving Total Elbow System, Biomet Orthopedics, Inc.

Latitude Total Elbow Prosthesis, Tornier, Inc. 2011.

Latitude Total Elbow Surgical Technique, Tornier, Inc.

The Sorbie-Questor Total Elbow System Surgical Technique, Wright Medical Technology Inc., 1997.

Total Elbow System Surgical Procedure, Solar Upper Extremity System, Howmedica Osteonics, 2000.

Zimmer Conrad/Morrey Total Elbow, Zimmer, Inc., 2009.

Adolfsson L, Nestorson J. The Kudo Humeral Component as Primary Hemiarthroplasty in Distal Humeral Fractures, J Shoulder Elbow Surg 2012;21 (4):451-455.

A. J. Donaldson, H. E. Thomson, N. J. Harper and N. W. Kenny. Bone cement implantation syndrome, BR J Anaesth 2009; 102: 12-22.

Bennett JB, Mehlhoff TL. Total Elbow Arthroplasty: Surgical Technique, J Hand Surg Am 2009;34 (5):933-939.

J. M. Brinkman et al., Failure Mechanisms in Uncemented Kudo Type 5 Elbow Prosthesis in Patients With Rheumatoid Arthritis, Ada Orthopaedica (2007) 78(2), 263-270.

(56) References Cited

OTHER PUBLICATIONS

K. J. Burkhart, G. Stein, E. Skooras, and L. P. Muller, Revisionsendoprothetik des Ellenbogens, Der Unfallchirurg (2010) 996-1005.
Burkhart KJ, Nijs S, Mattyasovszky SG et al. Distal Humerus Hemiarthroplasty of the Elbow for Comminuted Distal Humeral Fractures in the Elderly Patient, J Trauma 2011;71 (3): 635-642.
C. Spormann et al., Treatment Strategies for Periprosthetic Infections After Primary Elbow Anthroplasty, Journal of Shoulder and Elbow Surgery (2012) 21, 992-1000.
Cross MB, Sherman SL, Kepler CK et al. The Evolution of Elbow Arthroplasty: Innovative Solutions to Complex Clinical Problems, J Bone Joint Surg Am 2011;92 Suppl 2:98-104.
Dee R. Total Replacement Arthroplasty of the Elbow for Rheumatoid Arthritis, J Bone Joint Surg BR 1972;54 (1):88-95.
Duncan CP, Masri BA. Fractures of the Femur After Hip Replacement, Instr Course Lect 1995;44:293-304.

\* cited by examiner

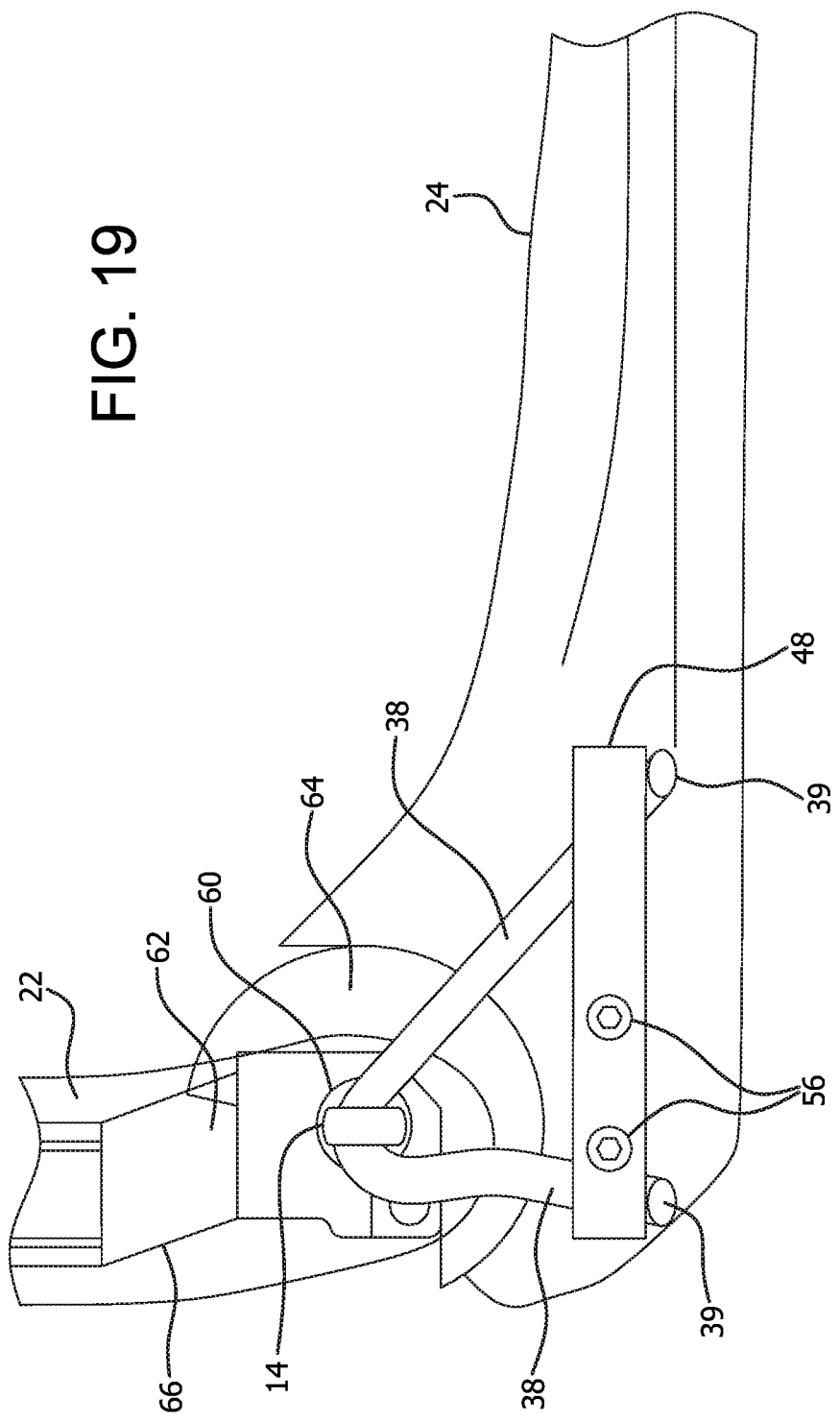

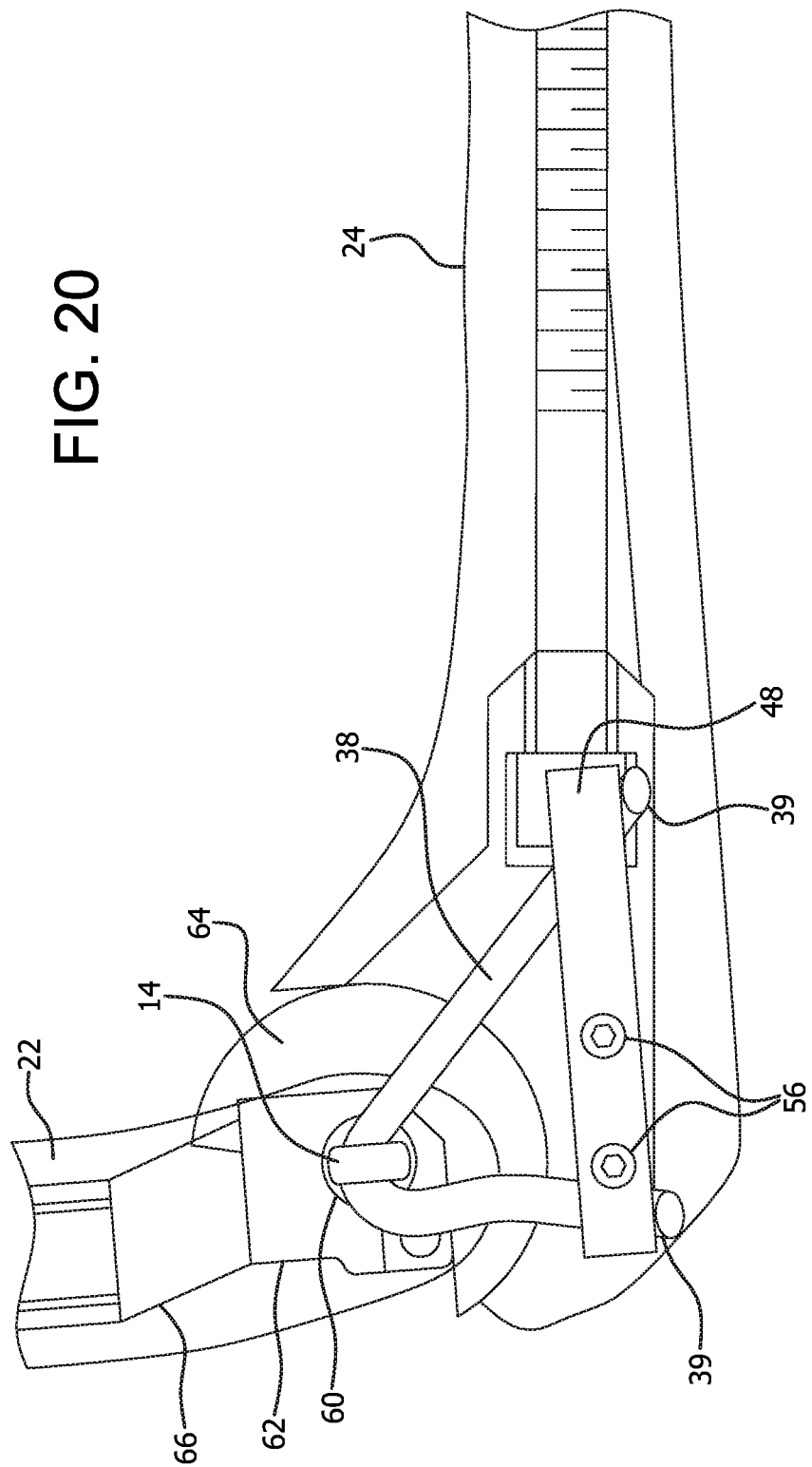

LIGAMENT RETENTION DEVICE

CROSS REFERENCE TO RELATED APPLICATION

This application claims the benefit of U.S. provisional patent application Ser. No. 62/619,899, filed Jan. 21, 2018, and entitled "Medial and Lateral Collateral Ligament Reconstruction System."

This application also expressly incorporates by reference the entire disclosures of U.S. Pat. No. 9,289,304, which was issued to Robert A. Kaufmann on Mar. 22, 2016, U.S. Pat. No. 9,962,200, which was issued to Robert A. Kaufmann on May 8, 2018, and US 2016/0158018, which was invented by Robert A. Kaufmann and published on Jun. 9, 2016.

TECHNICAL FIELD

This application relates to ligament reconstruction. More particularly, a system and method for medial and collateral ligament reconstruction is provided.

BACKGROUND INFORMATION

The human elbow consists of three bones that are connected by ligaments. The elbow is a hinge joint where the trochlea forms a convex, proximal surface, which articulates with the concave surface trochlear notch. Motion occurs in an essentially constrained manner about an ulno-humeral centerline of rotation.

The origin of the Medial Collateral Ligament (MCL) is on the anterior inferior margin of the epicondyle. With the elbow flexed 90 degrees, the anterior bundle of the MCL travels in a 45 degree direction from the anterior inferior margin of the epicondyle to the sublime tubercle of the ulna. The insertion is on the sublime tubercle of the ulna.

The origin of the LCL is the isometric point on the lateral condyle, which is determined by visually estimating the center of the circle that is partially defined by the circular shape of the capitellum when it is viewed directly from the lateral side. The tubercle on the supinator crest is exposed by subperiosteal elevation of the anconeus muscle.

The native elbow joint benefits from static and dynamic stabilizers that create a well constrained joint. The centerline of the trochlea can be considered representative for the centerline of ulnohumeral joint rotation. The major ligamentous contributors to varus and valgus elbow stability are the Lateral Ulnar collateral ligament (LUCL) and the Medial Collateral Ligament (MCL). Elbow collateral ligament integrity is paramount for ensuring joint stability.

These ligaments can become stretched or torn because of over-stressed movement or an injury. When the elbow becomes unstable, a ligament reconstruction is needed. Ligament reconstruction typically reestablishes joint stability through a bone-tendon connection. An autograft tendon is taken from another part of the body or an allograft tendon is taken from a cadaver and is woven through bone tunnels that have been drilled into the bones of the joint. The tendon graft is appropriately tensioned and then the tendons are secured to the bones of the joint. Most commonly, isolated reconstructions of either the Medial collateral Ligament (MCL) or the Lateral Collateral Ligament (LCL) are performed.

The Lateral Collateral Ligament is the primary restraint to varus forces across the elbow joint. It is formed by two bands, the radial collateral ligament (RCL) and the lateral ulnar collateral ligament (LUCL). The LUCL originates from the lateral epicondyle, and inserts on the supinator crest of the ulna. The LUCL has been considered to be the primary stabilizer, with disruption of the LUCL playing a crucial role in the development of posterolateral rotatory instability (PLRI). Reconstructive techniques for lateral sided instability have been described to address instability.

On the medial side, collateral ligament failure is seen most commonly in overhead throwing athletes, and is often associated with throwing performance deterioration. Repeated valgus stress placed on the elbow during the throwing motion creates ligamentous laxity. Reconstructive techniques for medial sided instability have been described to address instability.

Ligament insufficiency of both the MCL and LCL can lead to gross elbow instability, which requires reconstruction of both ligaments in one setting. Two similar techniques have been described to accomplish this goal. The methods described by van Riet et al and Finkbone simultaneously reconstruct the MCL and LCL using one graft. The Finkbone "box-loop" design passes the donor tendon through the humerus and ulna and ties back to itself, creating a loop. Good medium term results have been demonstrated for the Finkbone technique. These methods for bilateral ligament reconstruction require passing ligaments through bone. This is wasteful in that portions of the "box-loop" reside within the bones where they are not serving their purpose of transmitting force that occurs across the elbow. These techniques may be difficult to tension as the box-loop graft is tightened on either the medial or lateral sides but not both. These techniques have the potential for one side being tighter than the other, which, subsequently, may impart a torque to the elbow. Also, when tightening the ligament reconstruction on one side, it may be difficult to maintain elbow reduction.

An example of a presently existing system is disclosed in U.S. Pub. No. 2009/0228017 A1, which was published on Sep. 9, 2009 by Evan D Collins. This published application discloses a system for ligament reconstruction that uses jigs as drill guides to drill intersecting holes for the placement of ligament grafts that are employed for elbow stabilization purposes. The apparatus of this system has specially formed jigs placed over bones. Two intersecting holes are drilled in the ulna to form a single passageway, and a tendon graft is extended through the passageway. An oval hole is drilled into the humerus, and a pair of branch holes are drilled to intersect the closed end of the oval hole. A suture is attached to each end of the tendon. Each suture is threaded into the oval hole and then out one of the branch holes, so that the ends of the tendon are within the oval hole. A locking plug is placed in each branch hole to secure each suture within its branch hole, thereby securing the ends of the tendon within the oval hole.

U.S. Pat. No. 6,949,102 discloses a ligament reconstruction tensioning device The equal tension applying device is used to apply equal tension to a group of tendons. Tendon loops are fixed in a femoral tunnel with a fixation pin that extends into and through a tibial tunnel. The method includes the steps of: tying the ends of the sutures together to form a loop, placing a hook of the elongate tensioning device over the suture loop, applying tension on the device, followed by anchoring the ends of the tendon strands to the tibia.

U.S. Pat. No. 4,712,542, issued on Dec. 15, 1987 to Daniel et al., describes a method and instrument for skeletal-referenced isometric positioning and tensioning of a ligament graft, particularly during knee surgery involving the anterior cruciate and the posterior cruciate ligaments. The graft is extended from one fixation site and attached to a sled slidably carried by a frame which is skeletally mounted to the other fixation site. The sled slides to tension the graft. Isometry is achieved when the relative positions of the frame and sled indicate constant graft tension and displacement through the entire range of passive knee flexion. The sled can be fixed relative to the frame for evaluation of joint laxity.

U.S. Pat. No. 6,325,804, issued on Dec. 4, 2001 to Wenstrom Jr. et al., discloses a method for performing an anterior cruciate ligament repair procedure wherein a bone plug attached to a section of tendon or ligament is fixed in a bone tunnel. Longitudinal bone tunnels are drilled in the femur and tibia. A suture tunnel extends coaxially with the femoral tunnel, and terminates with an exit at the surface of the femur. A glue tunnel is drilled transversely to the femoral tunnel, and intersects the femoral tunnel's upper end. A femoral bone plug and tibial bone plug are secured to opposing ends of a tendon. A suture mounted to the femoral bone plug is threaded through the tibial tunnel, femoral tunnel, and suture tunnel. Glue or bone cement is injected into the glue hole, and then the femoral plug is pulled past the glue hole. The tibial bone plug is secured by screws, pins, or additional glue or bone cement.

U.S. Pat. No. 5,562,668, issued on Oct. 8, 1996 to Johnson, discloses a screw tensioning device for holding at least one end of a ligament graft. The device has a thimble which locates in the mouth of a hole drilled through bone, a nut captively seated in the thimble, and an anchorage element with a screw-threaded stud which can engage the nut. Different forms of anchorage elements are provided for different grafts, but each is adapted to securely hold one end of a ligament graft. The anchorage element with a ligament attached is drawn through the hole from the opposite side to the thimble until the stud engages the nut. The nut is then turned by a tool until the required tension is achieved.

U.S. Pat. No. 6,878,150 issued on Apr. 12, 2005 to McGuire et al., discloses a method for precisely forming bone tunnels in a cruciate ligament reconstruction of the knee. The method generally includes the steps of drilling a hole in one of the bones, using a femoral guide to determine the placement of the second tunnel, and drilling the second tunnel according to the position of the femoral guide. The femoral guide is cannulated.

U.S. Pat. No. 5,520,693, issued on May 28, 1996 to McGuire et al., discloses a device for forming bone tunnels in cruciate ligament reconstruction of the knee. The device has an elongate body that includes a cylindrical member and an arcuate surface extending from the cylindrical member. A lumen located in the body receives a guide wire. The lumen extends for the length of the cylindrical member through an opening formed on the arcuate surface so as to allow the guide wire to protrude from the elongate body. This allows the guide wire to contact the bone surface. A tongue located on the body is used to engage the edge of bone surface whereby the guide wire protruding from the body contacts the bone surface.

Since tendons used to reconstruct ligaments are often harvested from the patient's body, minimizing the amount of tendon that must be harvested is desirable. Additionally, providing a simple way to ensure that the tension of the reconstructed ligaments is properly balanced is desirable. Minimizing any unnecessary or undesired frictional or other forces against the reconstructed tendons is preferable. Simplification of the surgical procedures necessary for reconstructing ligaments is also desirable.

SUMMARY

The above needs are met by a ligament reconstruction device. The ligament reconstruction device has a body having a central portion and a pair of ends. Each end defines an opening therein. The opening is dimensioned and configured to receive an allograft or autograft ligament reconstruction member therethrough, The above needs are further met by a prosthetic joint. The prosthetic joint comprises a first bone portion. The first bone portion has a base having a condylar portion for interfacing with a condylar portion of an opposing bone, or with a condylar portion of a second bone portion of the prosthetic joint. The prosthetic joint further comprises a bone securing portion secured to the base. The bone securing portion is structured to interface with an intradedullary canal of a bone to secure the first bone portion to the bone. The base defines a hole therein, with the hole being substantially parallel to an axis of rotation of the prosthetic joint. The prosthetic joint further comprise a ligament reconstruction device. The ligament reconstruction device comprises a body having a central portion and a pair of ends. Each end defines an opening therein. The opening is dimensioned and configured to receive an allograft or autograft ligament reconstruction member therethrough. The body has a diameter that is substantially the same as the diameter of the hole. The ligament reconstruction device has a length that is substantially equal to or less than the length of the hole.

The above needs are also met by a method of reconstructing ligaments for a joint. The method comprises drilling a first hole through the first bone, with the first hole being substantially parallel to the axis of rotation of the joint. A ligament reconstruction device is provided. The ligament reconstruction device has a body having a central portion and a pair of ends. Each end defines an opening therein, with the opening being dimensioned and configured to receive an allograft or autograft ligament reconstruction member therethrough. The body has a diameter that is substantially the same as the diameter of the first hole. The ligament reconstruction device has a length that is substantially equal to or less than the length of the hole.

The method continues with providing a first allograft or autograft ligament reconstruction member and a second allograft or autograft ligament reconstruction member, with each ligament reconstruction member having a middle portion and a pair of ends. The first ligament reconstruction member is passed through one opening within one end of the ligament reconstruction device until the middle portion of the first ligament reconstruction member is disposed within the opening of the ligament reconstruction device. The other end of the ligament reconstruction device is inserted into the first hole until the opening at the other end of the ligament reconstruction device protrudes from the first hole, and the ligament reconstruction device is otherwise within the first hole. The second ligament reconstruction member is passed through the other opening within the other end of the ligament reconstruction device until the middle portion of the second ligament reconstruction member is disposed within the opening of the ligament reconstruction device. The ligament reconstruction member is moved so that the ligament reconstruction member is substantially completely contained within the first hole.

The method continues with drilling at least one second hole within the second bone, so that the at least one second hole is substantially parallel to the axis of rotation of the second bone around the joint. A pair of plates is provided, with each of the plates having a plate hole defined therein. At least one bolt or screw is provided, with the bolt or screw being dimensioned and configured to fit within the at least one second hole. A nut is provided, with the nut being structured to interface with the bolt or screw. The ends of the ligament reconstruction members are tensioned, and then placed over the second bone, with the ends of the ligament reconstruction members between the second bone and one of the two plates. Each bolt or screw is placed through the at least one second hole as well as the plate hole within each plate, and the nut is secured to each bolt or screw.

The above needs are further met by a method of reconstructing ligaments for a joint. The method comprises providing a prosthetic joint. The prosthetic joint comprises a first bone portion. The first bone portion has a base having a condylar portion for interfacing with a condylar portion of an opposing bone, or with a second bone portion of the prosthetic joint. The first bone portion further has a bone securing portion secured to the base. The bone securing portion is structured to interface with an intradedullary canal of a bone to secure the first bone portion to the bone. The base defines a first hole therein, with the first hole being substantially parallel to an axis of rotation of the prosthetic joint. The prosthetic joint further comprises a ligament reconstruction device. The ligament reconstruction device comprises a body having a central portion and a pair of ends, with each end defining an opening therein. Each opening is dimensioned and configured to receive an allograft or autograft ligament reconstruction member therethrough. The body has a diameter that is substantially the same as the diameter of the hole. The ligament reconstruction device has a length that is substantially equal to or less than the length of the hole.

The method continues with providing a first allograft or autograft ligament reconstruction member and a second allograft or autograft ligament reconstruction member, with each ligament reconstruction member having a middle portion and a pair of ends. The first ligament reconstruction member is passed through one opening within one end of the ligament reconstruction device until the middle portion of the first ligament reconstruction member is disposed within the opening of the ligament reconstruction device. The other end of the ligament reconstruction device is inserted into the first hole until the opening at the other end of the ligament reconstruction device protrudes from the first hole, and the ligament reconstruction device is otherwise within the first hole. The second ligament reconstruction member is passed through one opening within one end of the ligament reconstruction device until the middle portion of the second ligament reconstruction member is disposed within the opening of the ligament reconstruction device. The ligament reconstruction member is moved so that the ligament reconstruction member is substantially completely contained within the first hole.

The method continues with drilling at least one second hole within the second bone, with the at least one second hole being substantially parallel to the axis of rotation of the second bone around the joint. A pair of plates is provided, with each of the plates having a plate hole defined therein. At least one bolt or screw is provided, with the bolt or screw being dimensioned and configured to fit within the at least one second hole. A nut is provided, with the nut being structured to interface with the bolt or screw. The ends of the ligament reconstruction members are tensioned, and placed over the second bone with the ends of the ligament reconstruction members between the second bone and one plate. Each bolt or screw is placed through the at least one second hole as well as the plate hole within each plate. Each nut is secured to each bolt or screw.

These and other aspects of the invention will become more apparent through the following description and drawings.

BRIEF DESCRIPTION OF THE DRAWINGS

FIG. 19 is a cross-sectional front view of a prosthetic joint after installation for a hemiarthroplasty, showing a ligament reconstruction device being used in connection with the prosthetic joint, and also showing the ligament reconstruction members after they have been secured to the opposing bone.

FIG. 20 is a cross-sectional front view of a prosthetic joint after installation for a total arthroplasty. showing a ligament reconstruction device being used in connection with the prosthetic joint, and also showing the ligament reconstruction members after they have been secured to the opposing bone.

Like reference characters denote like elements throughout the drawings.

DETAILED DESCRIPTION

Figure 1:
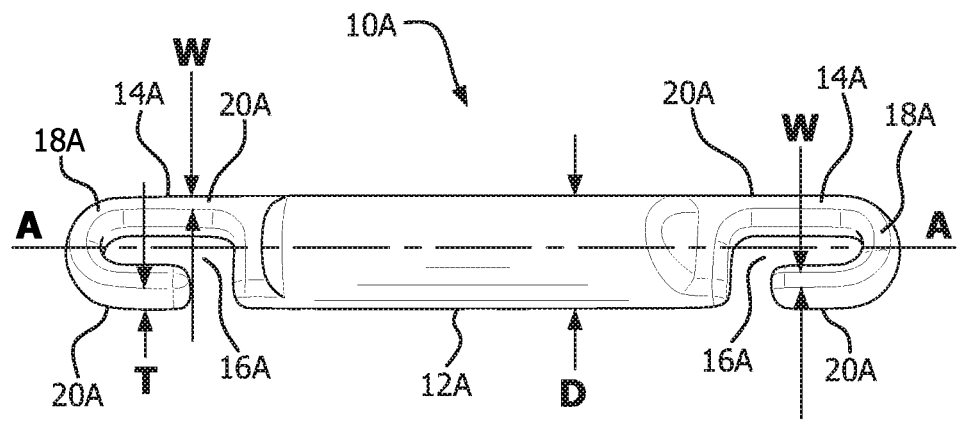
FIG. 1 is a perspective view of a ligament retention device.

Referring to the drawings, a ligament reconstruction device 10 is illustrated. The ligament reconstruction device 10 may be utilized to repair a joint, with or without the use of a prosthetic within the joint to be repaired. Regardless of whether a procedure is limited to ligament reconstruction of a natural elbow, or whether hemiarthroplasty or total arthroplasty is being performed, the goal is to substantially mimic the movement and stability of a natural joint through a system of ligament reconstruction. Joint stability is defined as the resistance to subluxation under physiologic stress and is the result of the mechanical interaction of the articular contours, the dynamic support of the investing musclotendinous units, and the static viscoelastic constraint of the capsuloligatmentous structures. Both the native elbow bony anatomy and the prosthetic elbow joint disclosed in U.S. Pat. No. 9,289,304 rely on the soft tissues to provide the necessary stability.

Collateral ligaments are complex structures whose individual fascicles are under differential tension and whose properties depend on joint position and load. The collateral ligaments of the elbow, by virtue of their medial and lateral locations, have a mechanical advantage in resisting medially and laterally directed forces that would cause joint subluxation. In an effort to gain joint visualization during arthroplasty surgery, these ligaments are detached and then re-inserted once the implants have been placed. Reattachment is difficult to do particularly when the ligament integrity is compromised such as in the joints of elderly patients. Patients suffering from post-traumatic arthritis often sustained soft tissue as well as bony trauma making a subsequent collateral ligament repair more tenuous. Therefore, tendons taken from the patient (autograft) or tendons taken from a donor of the same species (allograft) tendons are utilized as ligament reconstruction members, as described below.

Initially, tendons are selected for use in reconstructing the ligaments. The specific tendon or tendon portion selected are chosen because its loss will have minimal or no impact on the patient. Tendons that may be advantageously utilized include a longitudinal strip of triceps tendon or the Palmaris Longus tendon. Alternatively, toe extensors or the Plantaris tendon or even half of the Flexor Carpi Radialis tendon can be used. Allograft tendon material may also be utilized. The autograft or allograft tendons are referred to herein as ligament reconstruction members. The ligament reconstruction device 10 is intended to minimize the amount of tendon that must be taken from elsewhere in the patient or from a donor, as well as to improve the stability of the natural or prosthetic joint with which the device is used.

Figure 2A:
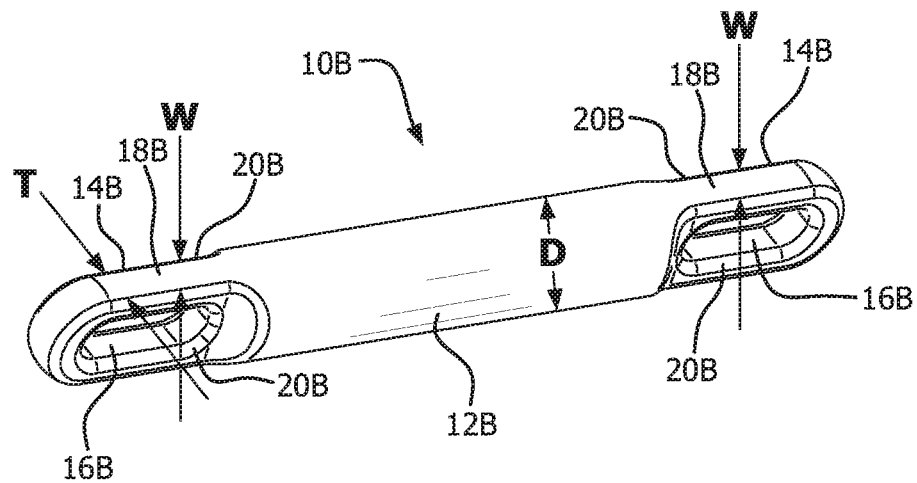
FIG. 2A is a perspective view of another ligament retention device.
Figure 2B:
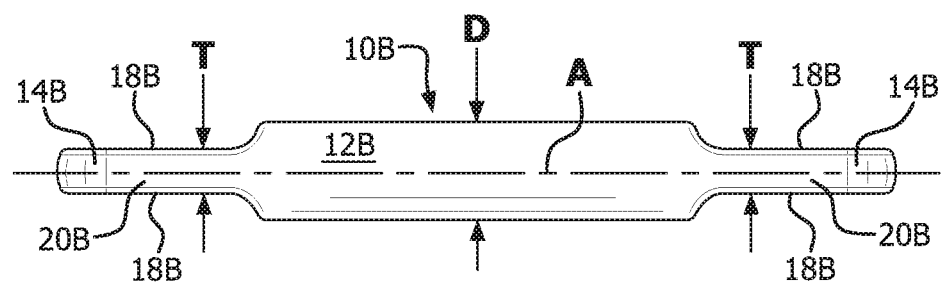
FIG. 2B is another perspective view of another ligament retention device.

The ligament reconstruction device 10 is illustrated in FIGS. 1 and 2. Within FIGS. 1 and 2, similar elements are given the same number, but components which differ in FIG. 1 are also denoted with an "A," and components which differ in FIG. 2 are also denoted with a "B." Whenever a reference character does not include an "A" or "B", it refers equally to both the device of FIGS. 1 and 2. The device 10A, 10B includes an elongated central body 12A, 12B. In the illustrated example, the central body 12A, 12B is generally cylindrical, so that it may fit within a generally round hole that may be drilled within a bone or provided within a prosthetic joint component. A hook 14A or a loop 14B is disposed at each end of the device 10A, 10B. The interior 16A, 16B of the hook 14A or loop 14B is dimensioned and configured to receive a ligament reconstruction member therethrough. Since a hook is nothing more than a loop with an open portion, the term "loop" as used herein shall refer to both the hook 14A and loop 14B examples unless a specific example is referenced. The hooks 14A and loops 14B include sides 18A, 18B, with edges 20A, 20B therebetween, having a width W and a thickness T. In the illustrated example, the width W is substantially equal to the diameter D of the central body 12. The thickness T is sufficiently smaller than the diameter D so that the sides are spaced inward from the edges of the central body 12A, 12B, in order to permit the presence of a ligament reconstruction member between the side walls 18A, 18B on either side of the hook 14A or loop 14B and the wall of the hole within the bone or prosthetic joint component. Towards this end, the hooks or loops 14A, 14B are disposed substantially along the central axis A of the device 10, providing substantially equal space to accommodate a ligament reconstruction member on either side of each hook 14A or loop 14B.

The overall length of the device 10, including both hooks 14A or loops 14B, is approximately the same length as or slightly shorter than the hole in which the device will be placed, so that any substantial protrusion of the device 10 from the hole is resisted, and the amount of allograft or autograft tendon that must be harvested to form each ligament reconstruction member is minimized. A length that is a small amount shorter than the hole within which the device 10 will be used provides for some flexibility in positioning the device 10 within the hole within which it is used, since it may move a short distance to equalize tension between the ligament reconstruction members on either side of the device without protruding from the hole.

Figure 3:
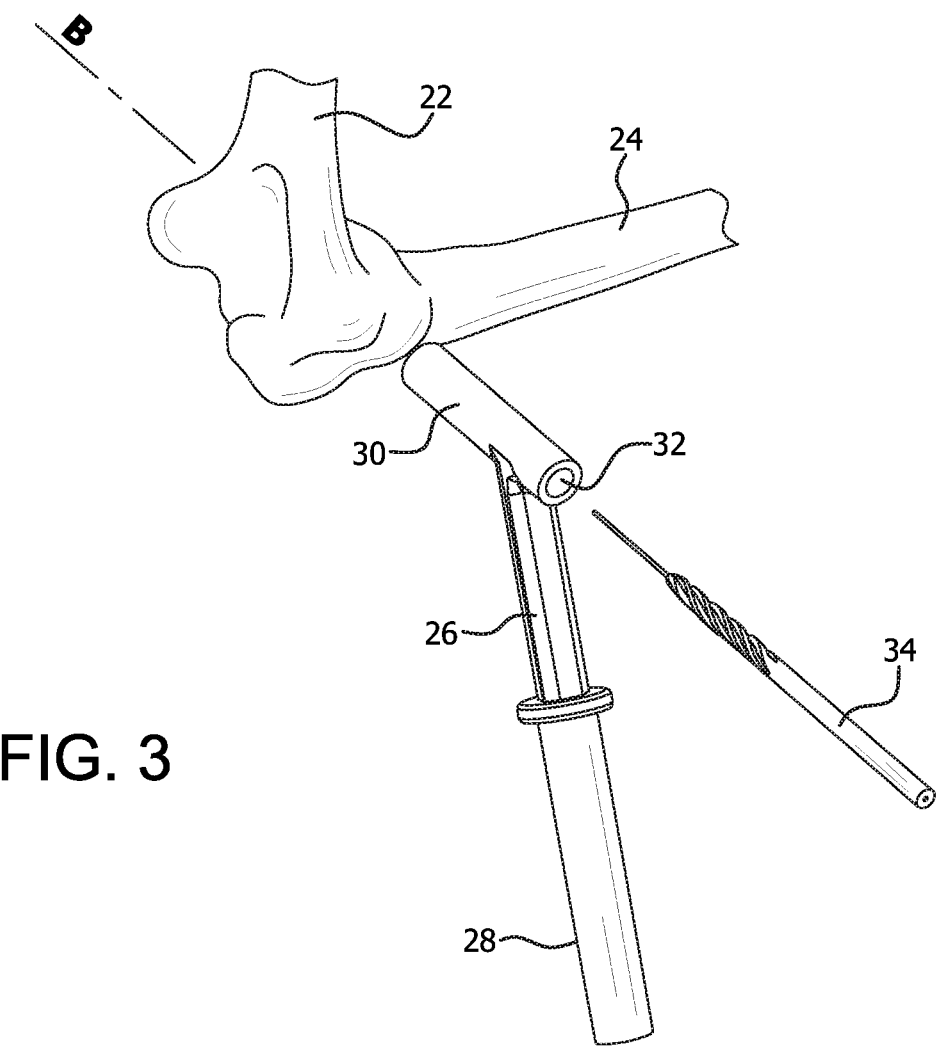
FIG. 3 is a perspective view showing a drilling operation for installation of the ligament retention device of FIG. 1 within one of two opposing bones forming a joint.

FIGS. 3-14 illustrate an example method of using the ligament retention device 10 in connection with a ligament reconstruction only that does not include installation of a prosthetic joint. In the illustrated example, an elbow joint is being repaired, and the MCL and LCL ligaments which connect the humerus 22 to the ulna 24 are being reconstructed. The first step of the method is illustrated in FIG. 3. In this step, a drill guide 26 having a handle 28 and guide shaft 30 with a guide hole 32 defined therethrough is positioned to drill a hole in one of the two bones forming the joint, with the hole in the illustrated example being drilled in a distal portion of the humerus, in close proximity to the condylar portion 27 of the humerus. Ideally, the hole 36 is located at a position wherein the radial distance between the central axis of the hole 36 in the condylar portion 46 of the ulna 24 remain substantially same throughout rotation of the joint. The drill 34 is then passed through the hole 32 and then completely through the humerus 22. The resulting hole 36 in the humerus is substantially aligned with the axis B of rotation of the bones forming the joint relative to each other, in this case the axis of rotation of the ulna around the condylar portion of the elbow. The drill 34 is also selected so that the hole 36 (FIG. 5) is also substantially the same diameter as the central body 12 of the ligament reconstruction device 10, so that the ligament reconstruction device 10 can be easily inserted therein, but will have substantially no play within the hole 36.

Figure 4:
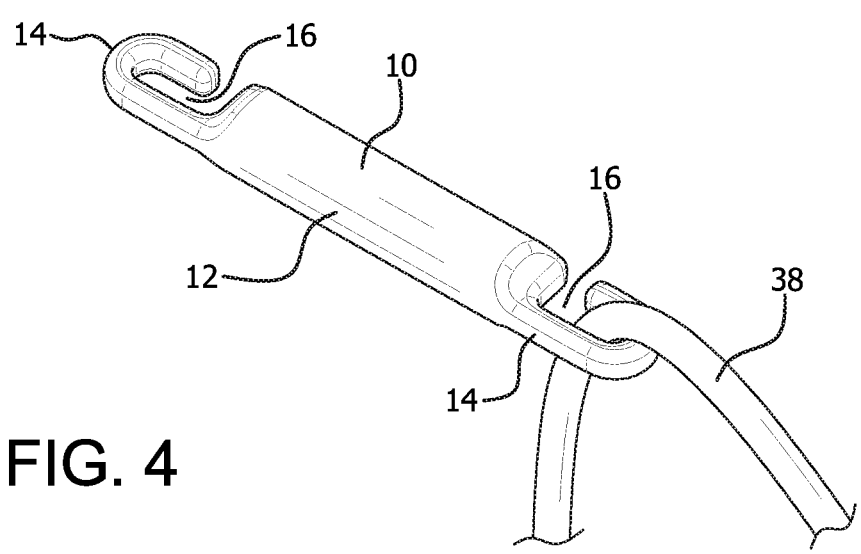
FIG. 4 is a perspective view of a tendon being placed within one end of a ligament retention device of FIG. 1.

FIG. 4 illustrates the placement of a ligament reconstruction member 38 within the interior 16 of one of the two loops 14 of the ligament reconstruction member 10 prior to inserting the ligament reconstruction member 10 into the hole 36 that has just been drilled into the humerus. Placing one of the two ligament reconstruction members 36 into the space 16 prior to insertion of the ligament reconstruction device 10 into the hole 36 simplifies the installation process. The ligament reconstruction member 38 is placed within the opening 16 until the ligament reconstruction member 38 is approximately centered within the opening 16.

Figure 5:
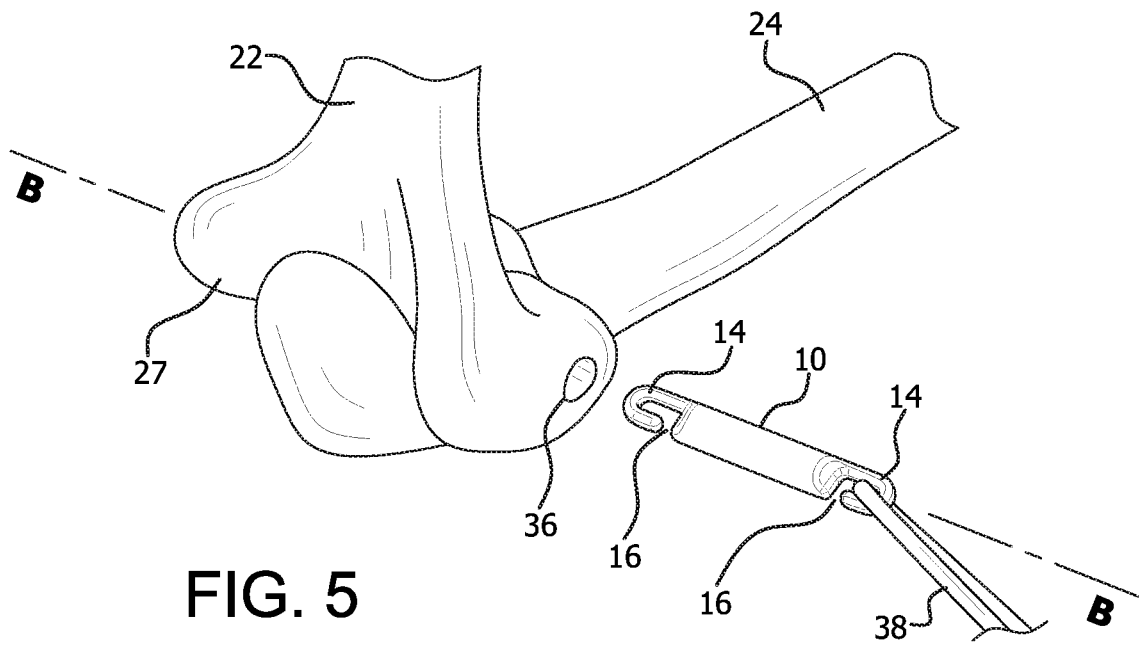
FIG. 5 is a perspective view of a ligament reconstruction device having a tendon held within one end prior to being positioned within a joint.
Figure 6:
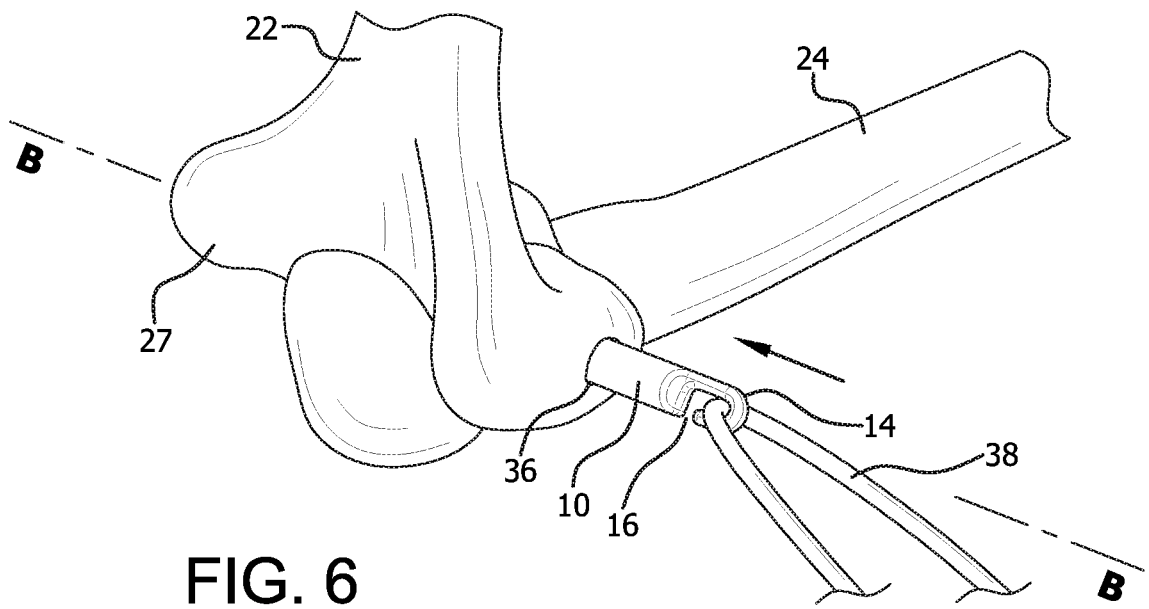
FIG. 6 is a perspective view of a ligament reconstruction device having a tendon held within one end being positioned within a joint.
Figure 7:
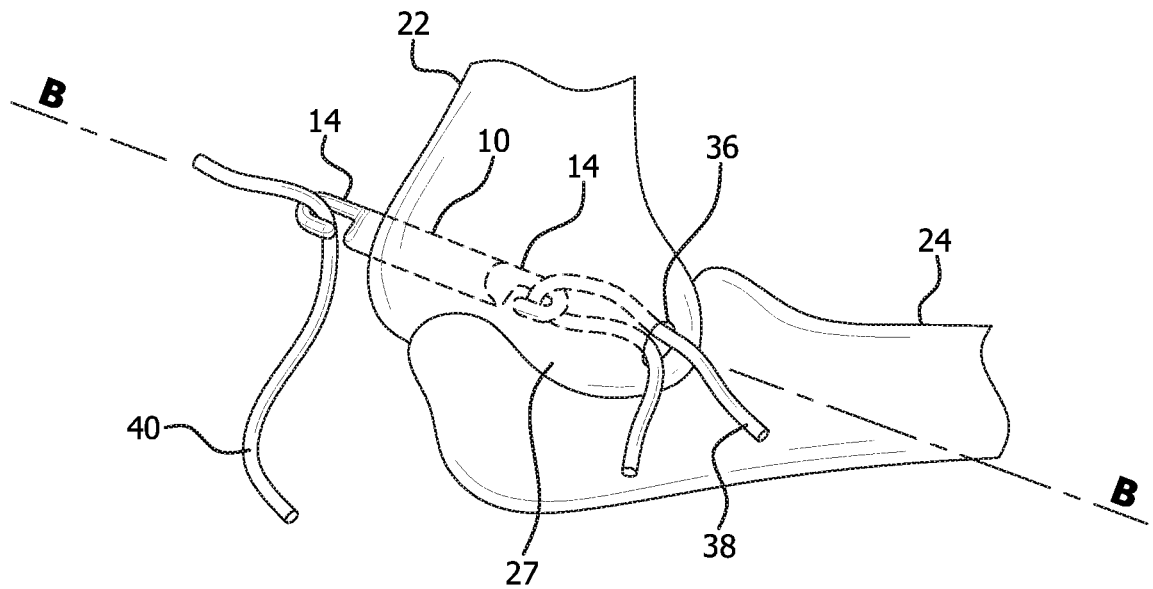
FIG. 7 is a perspective view of a second tendon being placed within the opposite end of a ligament retention device of FIG. 1 after positioning of the ligament retention device within a joint.
Figure 8:
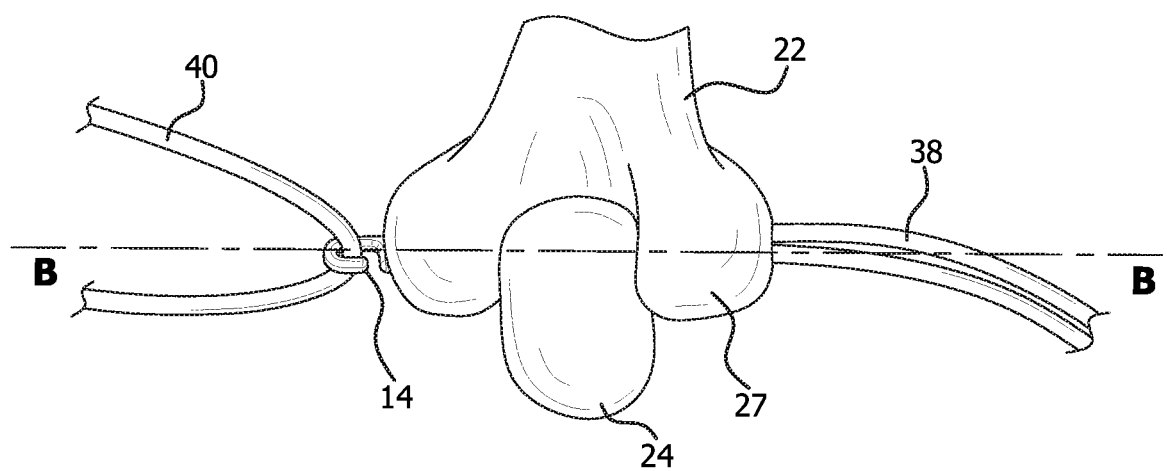
FIG. 8 is another perspective view of a second tendon being placed within the opposite end of a ligament retention device of FIG. 1 after positioning of the ligament retention device within a joint.

FIGS. 5-6 illustrate the insertion of the ligament reconstruction device 10 into the hole 36 that has been drilled into the humerus 22. The loop 14 through which the ligament reconstruction member 38 has not been inserted is the first portion of the ligament reconstruction device 10 to be inserted into the hole 36. This avoids the necessity of pulling the ligament reconstruction member 38 through the hole 36. The ligament reconstruction device 10 is pushed into the hole 36 until the empty loop 14 of the ligament reconstruction device 10 protrudes from the hole 36 sufficiently so that the opposing ligament reconstruction member 40 can be placed therein, as shown in FIGS. 7-8. Alternatively, the ligament reconstruction member 40 can be placed within one of the openings 16 prior to inserting the ligament reconstruction device 10 into the hole 36, and then the ligament reconstruction member 38 can be placed within the opposing loop 14 once the ligament reconstruction device 10 is within the hole 36.

Figure 9:
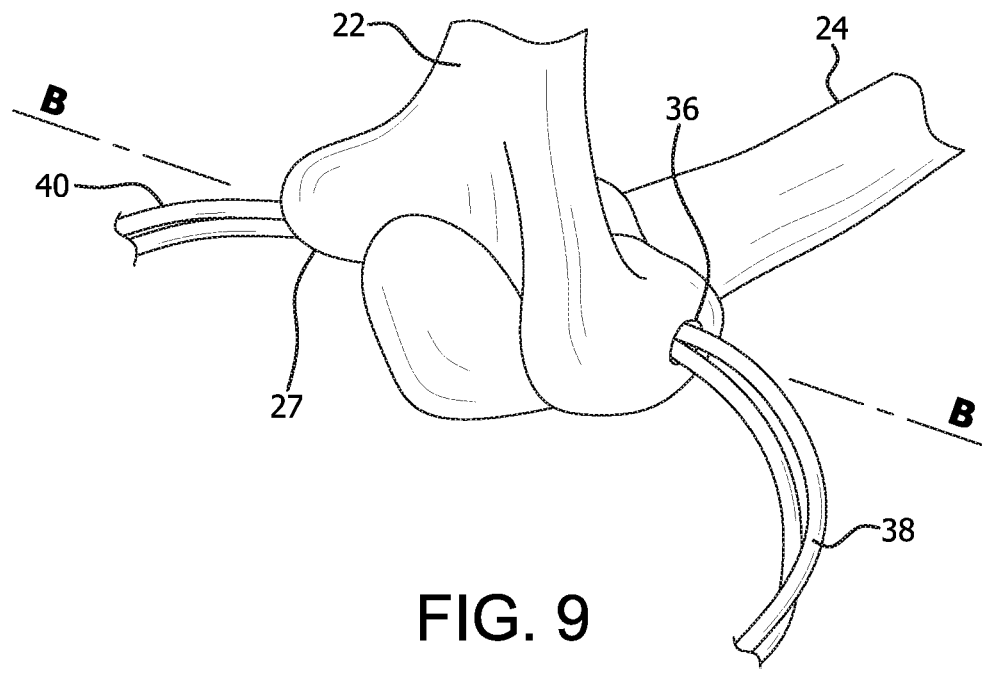
FIG. 9 is a perspective view of a joint after placement of the ligament reconstruction device of FIG. 1 and placement of tendons on either side of the ligament retention device.

Referring to FIG. 9, with both ligament reconstruction members 38, 40 now placed within the appropriate loop 14 of the ligament reconstruction member 10, the ligament reconstruction member 10 is pushed in the opposite direction into the hole 36, until the ligament reconstruction member 10 is approximately centered within the hole 36, and substantially completely contained within the hole 36. At this point, the ligament reconstruction members 38 can be tensioned, and the process of securing the ends to the opposing bone (in this case the ulna 24) can begin.

Figure 10:
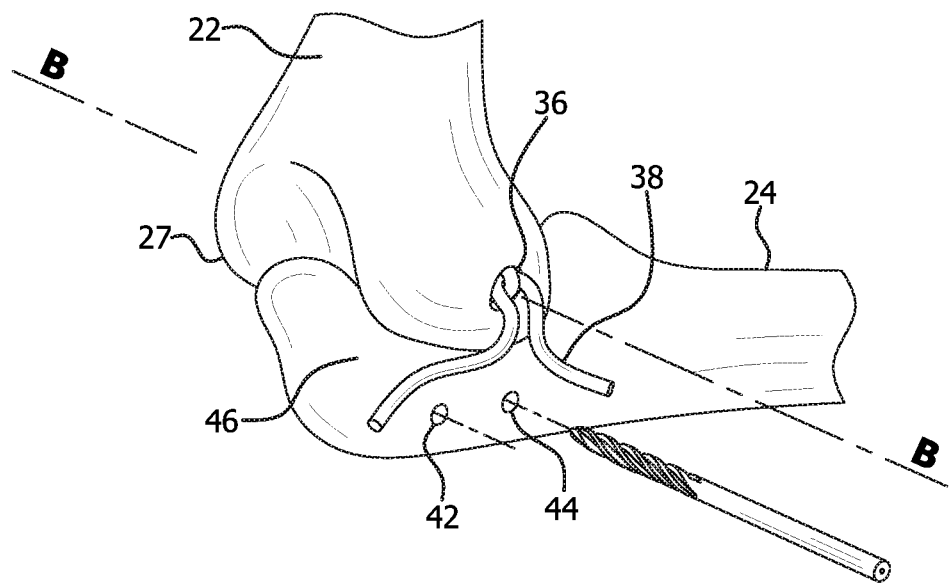
FIG. 10 is a perspective view of a drilling operation in preparation for securing the ends of the tendons to the opposing bone forming the joint.
Figure 11:
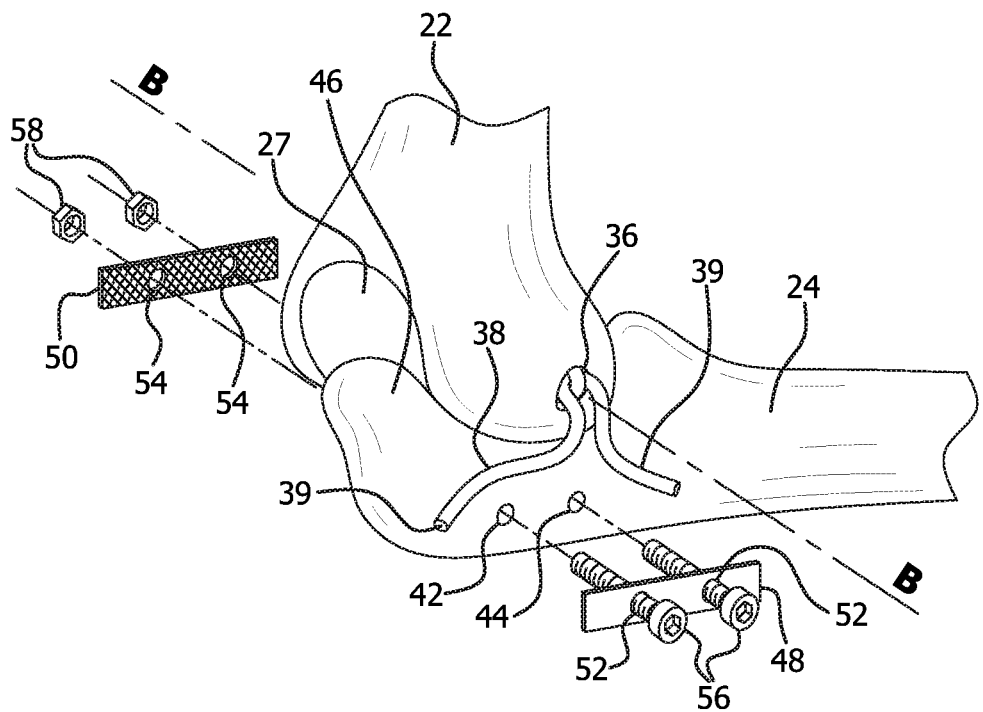
FIG. 11 is a perspective view of a ligament retention plate prior to installation on the opposing bone.
Figure 12:
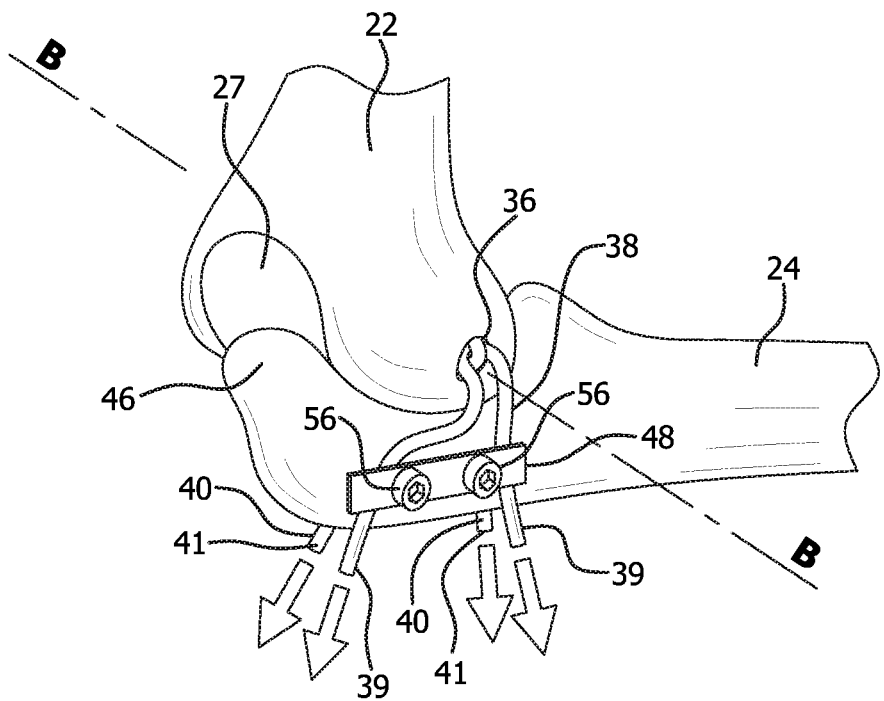
FIG. 12 is a perspective view of a joint after attachment of the ligament retention plate to the opposing bone.
Figure 13:
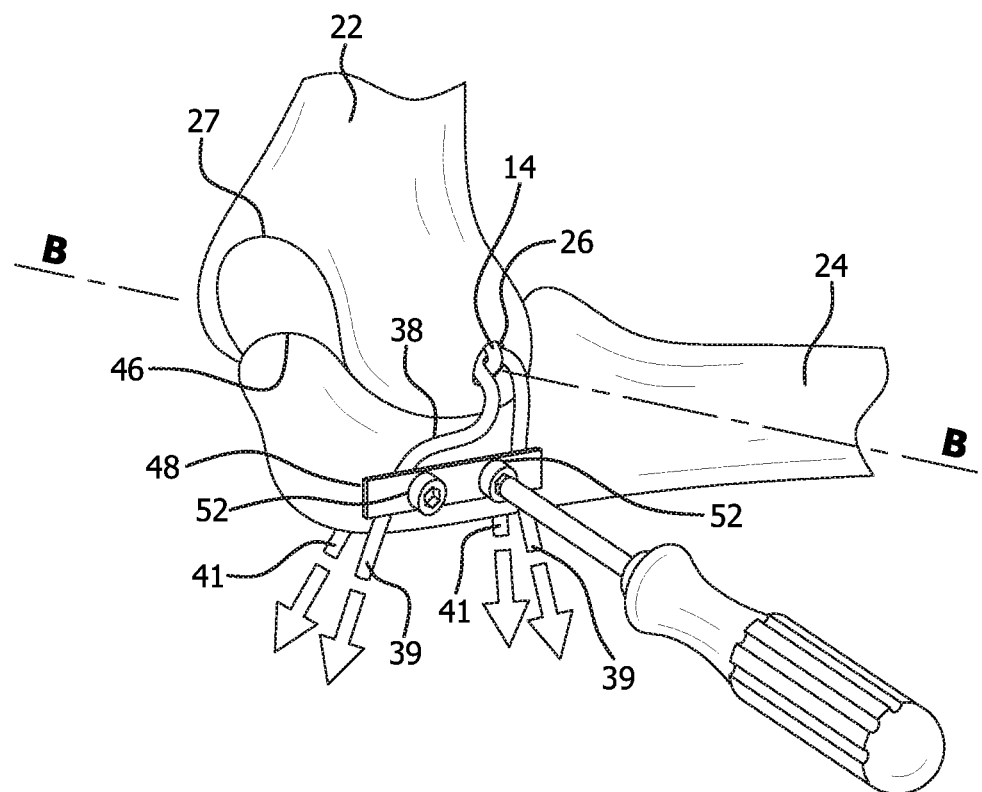
FIG. 13 is a perspective view of a joint showing tensioning of the ligament reconstruction members as well as securing the ends of the ligament reconstruction members between the retention plate and the opposing bone.
Figure 14:
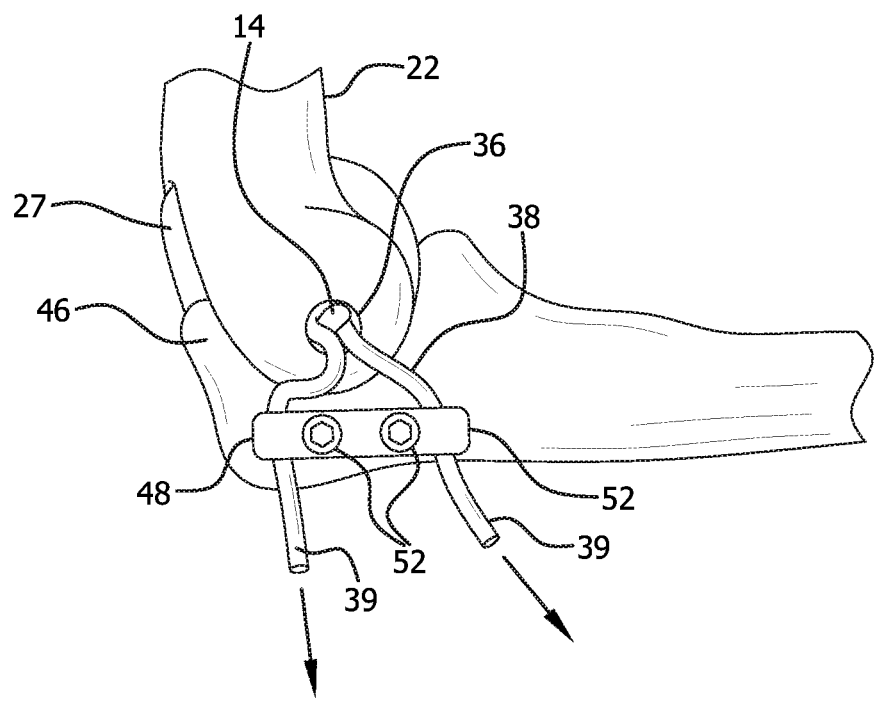
FIG. 14 is a side elevational view of a joint showing tensioning of the ligament reconstruction members as well as securing the ends of the ligament reconstruction members between the retention plate and the opposing bone.

Referring to FIG. 10, a pair of holes 42, 44 are drilled within the ulna 24 in close proximity to the condylar portion 46 of the ulna 24. The holes 42, 44 pass completely through the ulna 24. Next, referring to FIGS. 11-14, as the ligament reconstruction members 38, 40 are tensioned and held in their desired location, a pair of plates 48, 50 are secured over the ends of the ligament reconstruction members 38, 40. Although applying substantially equal tension to the ligament reconstruction members 38, 40 is desired, the device 10 may shift slightly within the hole 36 to equalize the tension if any variations in tension exist. Each of the plates 48, 50 defines a pair of holes 52, 54 therein. A pair of bolts or screws 56 are each passed through one of the holes 52, 54, through one of the holes 42, 44 in the ulna 24, and then through one of the holes 52, 54 in the opposing plate 48, 50. A nut 58 is secured to the end of each bolts or screw 56, and the bolts 56 are tightened in order to retain the ends 39, 41 of the ligament reconstruction members 38, 40 in their desired position. Over time, as the ligament reconstruction heals, the ligament reconstruction members 38, 40 will become adhered to the ulna 24.

Figure 15:
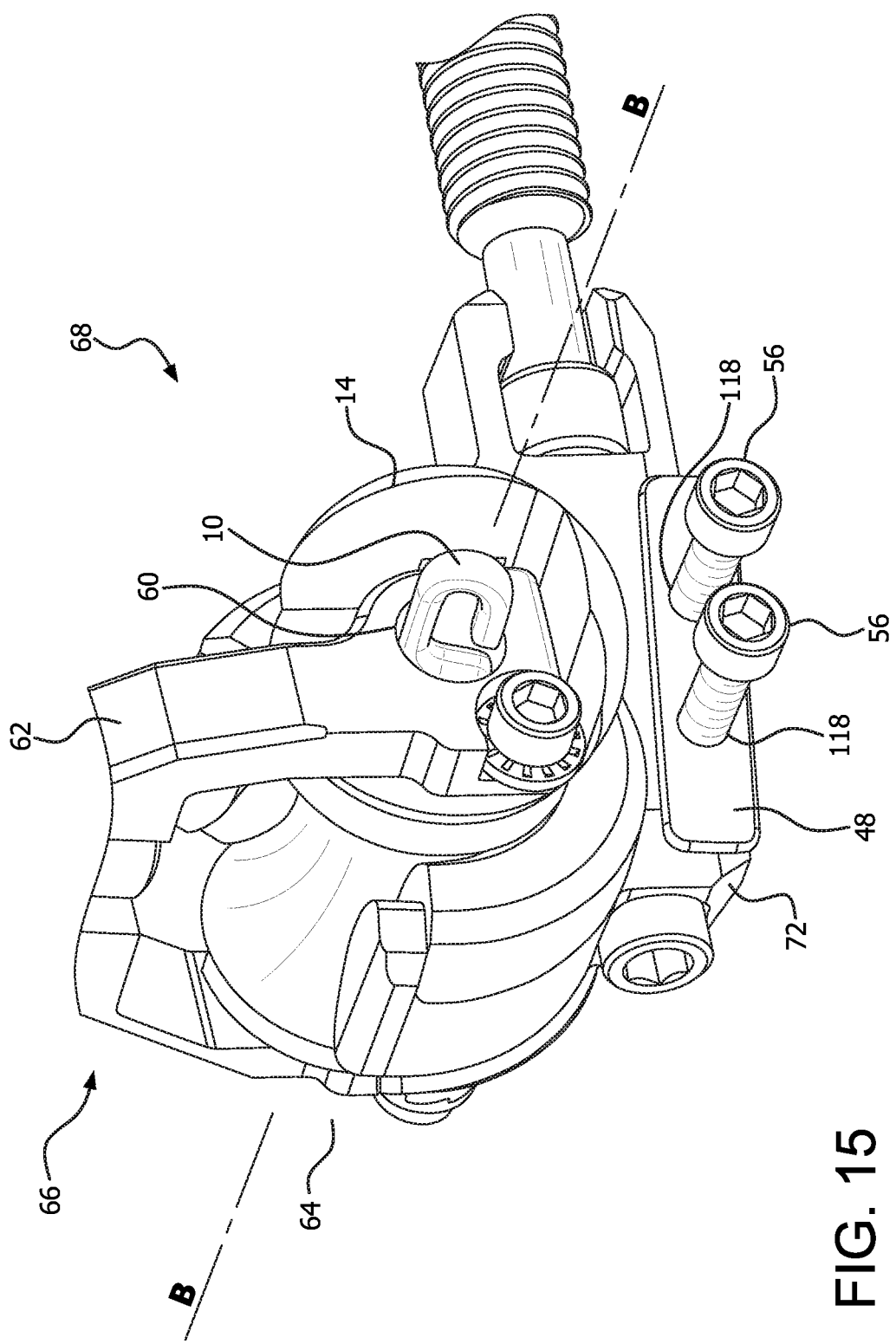
FIG. 15 is a perspective view of a prosthetic joint having a ligament reconstruction device of FIG. 1 installed therein.
Figure 16:
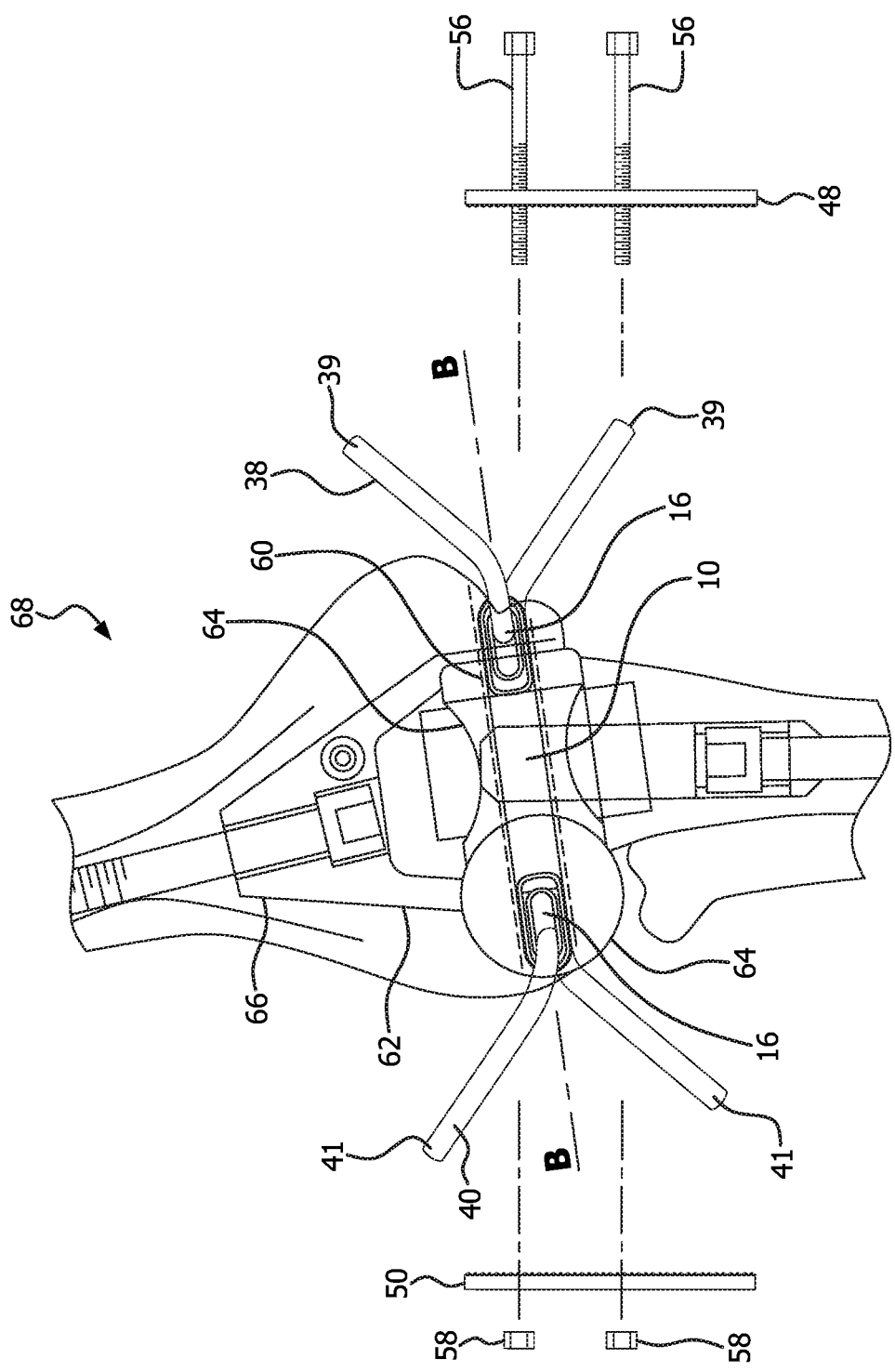
FIG. 16 is a cross-sectional side view of a ligament reconstruction device being used in connection with a prosthetic joint, showing the ligament reconstruction members placed within the ligament reconstruction device.
Figure 17:
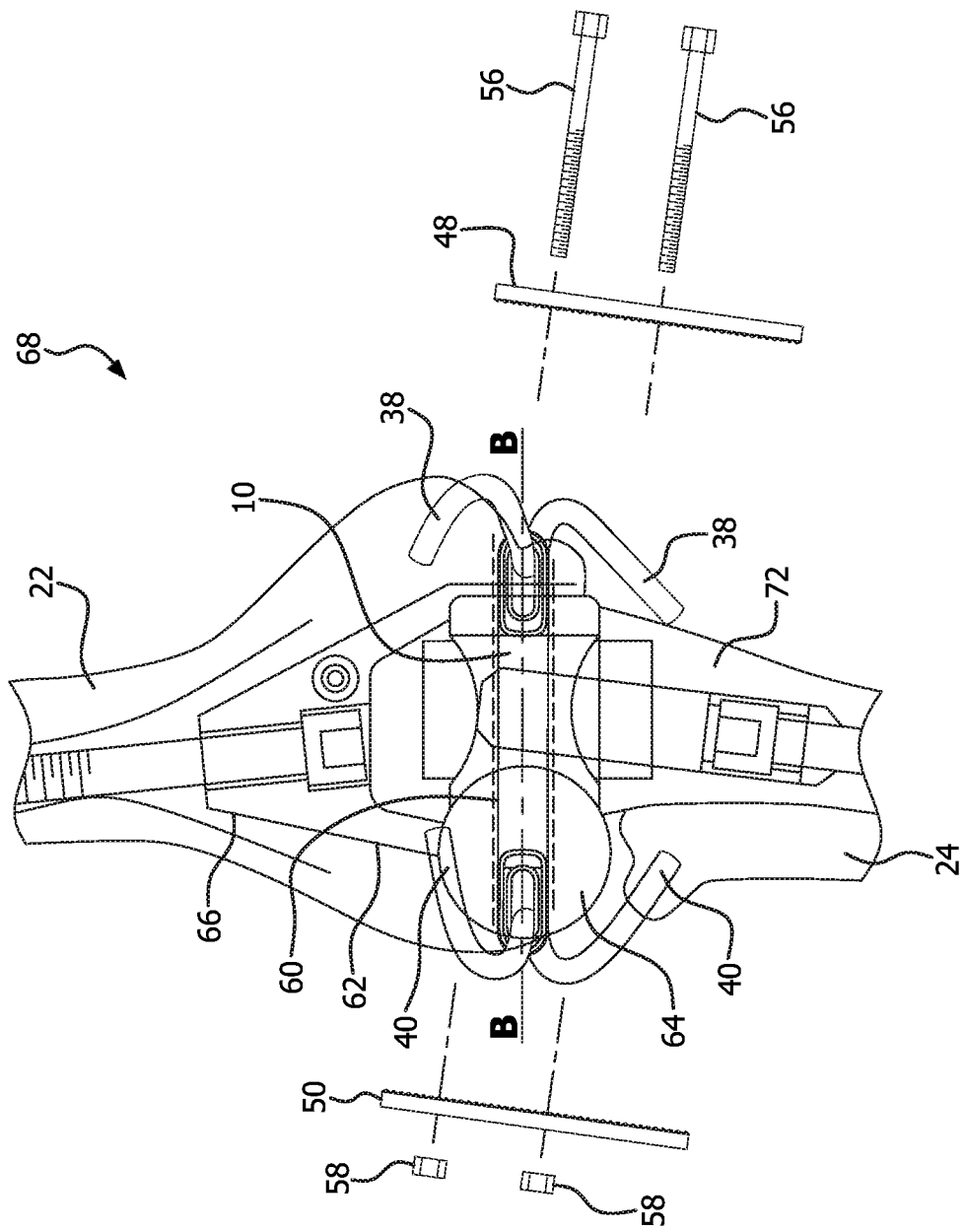
FIG. 17 is a cross-sectional side view of a ligament reconstruction device being used in connection with a prosthetic joint, showing the attachment of ligament reconstruction members to the opposing bone.
Figure 18:
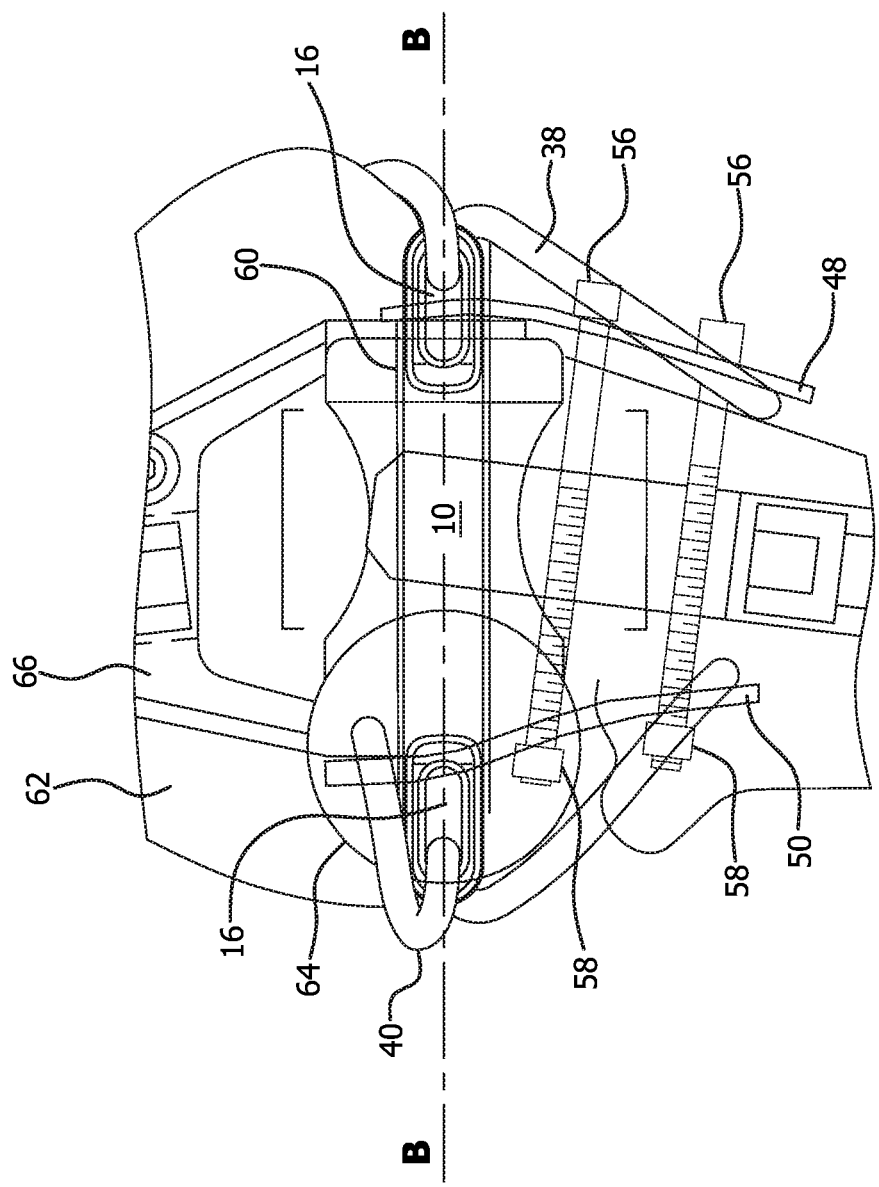
FIG. 18 is a cross-sectional side view of a ligament reconstruction device being used in connection with a prosthetic joint, showing the ligament reconstruction members after they have been secured to the opposing bone.

The method described above can be used not only directly with bone, but also with prosthetic elbow components. A prosthetic elbow, for example, the prosthetic elbow disclosed by U.S. Pat. No. 9,289,304, which was issued to Robert A. Kaufmann on Mar. 22, 2016, can benefit from the use of the ligament reconstruction device 10, and the disclosure of this patent is expressly incorporated herein by reference. FIGS. 16-20 herein reproduce FIGS. 17-21 of U.S. Pat. No. 9,289,304, with modifications to illustrate the use of the ligament reconstruction device 10. In the example of the prosthetic elbow of U.S. Pat. No. 9,289,304, a channel formed by the holes 55, 57 (FIGS. 1, 2, 11, and 17-22 of U.S. Pat. No. 9,289,304) of the yoke 28 and hole 53 of the spool 46 ((FIGS. 1, 4, 11, and 17-22 of U.S. Pat. No. 9,289,304) forms an optimal location for the ligament reconstruction device 10 disclosed herein, and the ligament reconstruction device 10 can be dimensioned and configured to fit within this channel, as illustrated in FIG. 15. Since this channel is formed within the humoral component 12, and because most hemiarthroplasties involve reconstruction of the condylar portion of the humerus rather than the ulna, the ligament reconstruction device 10 can be used within either a hemiarthroplasty or total arthroplasty. Although use of the full prosthetic for a total arthroplasty is illustrated in FIGS. 15-18 and 20, the procedural steps for reconstructing ligaments for hemiarthroplasty and for total arthroplasty are exactly the same for the humerus, and very similar for the ulna, with only one minor difference as described in greater detail below.

Referring to FIGS. 16-20, the ligament reconstruction device 10 is shown positioned within a hole 60, which as described above is formed by the yoke 62 and the spool 64 of the humeral component 66 of the prosthetic joint 68. This channel is substantially parallel to the axis of rotation B of the prosthetic joint. The ligament reconstruction members 38, 40 have been positioned within the openings 16 of the ligament reconstruction device 10 in the same manner as described above and illustrated in FIGS. 5-9. Specifically, one ligament reconstruction member 38, 40 is placed within one opening 16 of the device 10 so that the ligament reconstruction member 38, 40 is approximately centered within the opening 16. The other of the openings 16 is then pushed through the hole 60 until the empty opening 16 protrudes from the other side of the humeral component 66, and the remainder of the device 10 is within the hole 60. The other ligament reconstruction member 38, 40 is placed within the now-protruding opening 16 so that the ligament reconstruction member 38, 40 is approximately centered within the opening 16. The ligament reconstruction device 10 is then approximately centered within the hole 60.

Holes 42 are drilled in the ulna 24, also substantially parallel to the axis of rotation B of the prosthetic joint. In the case of a hemiarthroplasty (FIG. 19), the procedure for drilling the holes 42, 44 is exactly as described above. In the event of a total arthroplasty (FIGS. 16-18 and 20), the holes 42 are aligned with pre-existing holes in the ulnar component of the prosthetic joint, such as holes 118 defined within the base 72 as shown in FIG. 4 of U.S. Pat. No. 9,289,304. The ends 39, 41 of the ligament reconstruction members 38, 40 are tensioned, and are then placed under the plates 48, 50. Each of the bolts 56 are passed through one set of holes 52, 54 within one of the plates 48, 50, through one of the holes 42, 44, and then through the other of the holes 52, 54 within the other of the plates 48, 50. A nut 58 is then secured to the end of each bolts 56. The ends 39, 41 of the ligament reconstruction members 38, 40 are held in tension as the bolts 56 are tightened with in the nuts 58, thus securing the ends 39, 41 of the ligament reconstruction members 38, 40 against the ulna 24. Regardless of whether hemiarthroplasty or total arthroplasty is performed, the ends 39, 41 of the ligament reconstruction members 38, 40 will heal into adhesion with the ulna 24.

The present invention therefore provides a ligament reconstruction device and method that may be used in connection with simple ligament repair, hemiarthroplasty, or total arthroplasty. The device and method minimizes the amount of allograft or autograft tendons that must be harvested in order to provide ligament reconstruction members. Because the device is free to slide within the hole within which it is positioned (within the constraints of the ligament reconstruction members attached thereto), the device and method also balances the tension on either side of the joint with which the device is used, thus improving the stability of the joint.

A variety of modifications to the above-described embodiments will be apparent to those skilled in the art from this disclosure. In particular, although the device and method are described using the example of an elbow joint, the present invention can be used to repair other joints without departing from the scope of the invention. Thus, the invention may be embodied in other specific forms without departing from the spirit or essential attributes thereof. The particular embodiments disclosed are meant to be illustrative only and not limiting as to the scope of the invention. The appended claims, rather than to the foregoing specification, should be referenced to indicate the scope of the invention.

What is claimed is:

1. A ligament reconstruction device, comprising: a body having a central portion and a pair of ends, each end defining an opening therein, each opening being dimensioned and configured to receive an allograft or autograft ligament reconstruction member therethrough, the ends being disposed along a central axis of the ligament reconstruction member, the ends defining a width and a thickness, the width being substantially equal to a width or diameter of the central portion, the thickness that is sufficiently smaller than the width or diameter of the central portion so that an autograft or allograft ligament reconstruction member disposed on either side of one end can be accommodated without protruding beyond the width or diameter of the central portion.

2. A ligament reconstruction device, comprising:
a body having a central portion and a pair of ends, each end defining an opening therein, each opening being dimensioned and configured to receive an allograft or autograft ligament reconstruction member therethrough,
wherein the ligament reconstruction member defines a central axis;
the body is generally cylindrical; and
the ends define a width and a thickness, the width being substantially equal to a diameter of the central portion, the thickness that is sufficiently smaller than the diameter of the central portion so that an autograft or allograft ligament reconstruction member disposed on either side of one end can be accommodated without protruding beyond the diameter of the central portion.

3. A prosthetic joint, comprising:
a first bone portion, the first bone portion having:
a base having a condylar portion for interfacing with a condylar portion of an opposing bone, or with a second bone portion of the prosthetic joint;
a bone securing portion secured to the base, the bone securing portion being structured to interface with an intramedullary canal of a bone to secure the first bone portion to the bone;
the base defining a hole therein, the hole being substantially parallel to an axis of rotation of the prosthetic joint;
a ligament reconstruction device, comprising a body having a central portion and a pair of ends, each end defining an opening therein, each opening being dimensioned and configured to receive an allograft or autograft ligament reconstruction member therethrough, the body having a diameter that is substantially the same as the diameter of the hole, the ligament reconstruction device having a length that is substantially equal to or less than the length of the hole.

4. The prosthetic joint according to claim 3, wherein the body is generally cylindrical.

5. The prosthetic joint according to claim 3, wherein the ends are disposed along a central axis of the ligament reconstruction member, the ends defining a width and a thickness, the width being substantially equal to a width or diameter of the central portion, the thickness that is sufficiently smaller than the width or diameter of the central portion so that an autograft or allograft ligament reconstruction member disposed on either side of one end can be accommodated without protruding beyond the width or diameter of the central portion.

6. The prosthetic joint according to claim 3, wherein:
the ligament reconstruction member defines a central axis;
the body is generally cylindrical; and
the ends define a width and a thickness, the width being substantially equal to a diameter of the central portion, the thickness that is sufficiently smaller than the diameter of the central portion so that an autograft or allograft ligament reconstruction member disposed on either side of one end can be accommodated without protruding beyond the diameter of the central portion.

7. A method of reconstructing ligaments for a joint, the joint having a first bone, a second bone, and an axis of rotation of the second bone around the joint, the method comprising:
drilling a first hole through the first bone, the first hole being substantially parallel to the axis of rotation of the joint, the hole having a length and a diameter;
providing a ligament reconstruction device, the ligament reconstruction device having a body having a central portion and a pair of ends, each end defining an opening therein, each opening being dimensioned and configured to receive an allograft or autograft ligament reconstruction member therethrough, the body having a diameter that is substantially the same as the diameter of the first hole, the ligament reconstruction device having a length that is substantially equal to or less than the length of the hole;
providing a first allograft or autograft ligament reconstruction member and a second allograft or autograft ligament reconstruction member, each ligament reconstruction member having a middle portion and a pair of ends;
passing the first ligament reconstruction member through one opening within one end of the ligament reconstruction device until the middle portion of the first ligament reconstruction member is disposed within the opening of the ligament reconstruction device;
inserting the other end of the ligament reconstruction device into the first hole until the opening at the other end of the ligament reconstruction device protrudes from the first hole, and the ligament reconstruction device is otherwise within the first hole;
passing the second ligament reconstruction member through one opening within one end of the ligament reconstruction device until the middle portion of the second ligament reconstruction member is disposed within the opening of the ligament reconstruction device;
moving the ligament reconstruction member so that the ligament reconstruction member is substantially completely contained within the first hole;
drilling at least one second hole within the second bone, the at least one second hole being substantially parallel to the axis of rotation of the second bone around the joint;
providing a pair of plates, each of the plates having a plate hole defined therein;
providing at least one bolt or screw dimensioned and configured to fit within the at least one second hole, and a nut structured to interface with the bolt or screw;
tensioning the ends of the ligament reconstruction members;
placing the ends of the ligament reconstruction members over the second bone with the ends of the ligament reconstruction members between the second bone and one plate;
placing each bolt or screw through the at least one second hole as well as the plate hole within each plate; and
securing each nut to each bolt or screw.

8. A method of reconstructing ligaments for a joint, the joint having a first bone, a second bone, and an axis of rotation of the second bone around the joint, the method comprising:
providing a prosthetic joint, the prosthetic joint comprising:
a first bone portion, the first bone portion having:
a base having a condylar portion for interfacing with a condylar portion of an opposing bone, or with a second bone portion of the prosthetic joint;
a bone securing portion secured to the base, the bone securing portion being structured to interface with an intramedullary canal of a bone to secure the first bone portion to the bone;
the base defining a first hole therein, the first hole being substantially parallel to an axis of rotation of the prosthetic joint;
a ligament reconstruction device, comprising a body having a central portion and a pair of ends, each end defining an opening therein, each opening being dimensioned and configured to receive an allograft or autograft ligament reconstruction member therethrough, the body having a diameter that is substantially the same as the diameter of the hole, the ligament reconstruction device having a length that is substantially equal to or less than the length of the hole;
providing a first allograft or autograft ligament reconstruction member and a second allograft or autograft ligament reconstruction member, each ligament reconstruction member having a middle portion and a pair of ends;
passing the first ligament reconstruction members through one opening within one end of the ligament reconstruction device until the middle portion of the first ligament reconstruction member is disposed within the opening of the ligament reconstruction device;
inserting the other end of the ligament reconstruction device into the first hole until the opening at the other end of the ligament reconstruction device protrudes from the first hole, and the ligament reconstruction device is otherwise within the first hole;
passing the second ligament reconstruction member through one opening within one end of the ligament reconstruction device until the middle portion of the second ligament reconstruction member is disposed within the opening of the ligament reconstruction device;
moving the ligament reconstruction member so that the ligament reconstruction member is substantially completely contained within the first hole;
drilling at least one second hole within the second bone, the at least one second hole being substantially parallel to the axis of rotation of the second bone around the joint;
providing a pair of plates, each of the plates having a plate hole defined therein;
providing at least one bolt or screw dimensioned and configured to fit within the at least one second hole, and a nut structured to interface with the bolt or screw;
tensioning the ends of the ligament reconstruction members;
placing the ends of the ligament reconstruction members over the second bone with the ends of the ligament reconstruction members between the second bone and one plate;
placing each bolt or screw through the at least one second hole as well as the plate hole within each plate; and
securing each nut to each bolt or screw.

9. The method according to claim 8, wherein:
the prosthetic joint includes a second bone portion, the second bone portion comprising:
a base having a condylar portion for interfacing with the condylar portion of the first bone portion of the prosthetic joint;
a bone securing portion secured to the base, the bone securing portion being structured to interface with an intramedullary canal of a bone to secure the second bone portion to the bone;
the base defining at least one second hole therein, the at least one second hole being substantially parallel to an axis of rotation of the prosthetic joint; and
the step of drilling at least one second hole within the second bone includes aligning the at least one second hole within the second bone with the at least one second hole within the base.

* * * * *